United States Patent
Virtanen (10) Patent No.: US 6,328,032 B1
(45) Date of Patent: *Dec. 11, 2001

(54) INHALATION DEVICE

(75) Inventor: Risto Virtanen, Nurmijärvi (FI)

(73) Assignee: Astra Aktiebolag, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/068,384

(22) Filed: May 8, 1998

Related U.S. Application Data (63) Continuation of application No. PCT/SE98/00462, filed on Mar. 13, 1998.

(30) Foreign Application Priority Data

Mar. 14, 1997 (SE) .................................................... 9700944

(51) Int. Cl.$^7$ ........................ A61M 15/00; A61M 16/00; B05D 7/14; B65D 83/06
(52) U.S. Cl. ...................................................... 128/203.15
(58) Field of Search ........................ 128/203.12, 203.15, 128/205.12; 604/58

(56) References Cited

U.S. PATENT DOCUMENTS

| | | | |
|---|---|---|---|
| 4,668,218 | * 5/1987 | Virtanen | 604/58 |
| 4,805,811 | * 2/1989 | Wetterlin | 222/337 |
| 5,113,855 | * 5/1992 | Newhouse | 128/203.12 |
| 5,201,308 | * 4/1993 | Newhouse | 128/203.15 |
| 5,394,868 | * 3/1995 | Ambrosio et al. | 128/203.15 |
| 5,687,710 | * 11/1997 | Ambrosio et al. | 128/203.15 |
| 5,740,792 | * 4/1998 | Ashley et al. | 128/203.15 |
| 5,778,873 | * 7/1998 | Braithwaite | 128/203.15 |
| 5,829,434 | * 11/1998 | Ambrosio et al. | 128/203.15 |
| 5,924,417 | * 7/1999 | Braithwaite | 128/203.15 |

FOREIGN PATENT DOCUMENTS

| | | |
|---|---|---|
| 44 15 462 C1 | 8/1995 | (DE) . |
| 0 237 507 | 9/1987 | (EP) . |
| 0 520 440 A1 | 12/1992 | (EP) . |
| WO 95/29723 | * 11/1995 | (WO) ............................ 128/203.15 |
| WO95/32752 | 12/1995 | (WO) . |
| WO96/16687 | 6/1996 | (WO) . |

OTHER PUBLICATIONS

International Search Report.

* cited by examiner

*Primary Examiner*—John G. Weiss
*Assistant Examiner*—Joseph F. Weiss, Jr.
(74) *Attorney, Agent, or Firm*—Fish & Richardson P.C.

(57) ABSTRACT

An inhaler for administering powder by inhalation and a method of constructing the same, the inhaler including a member that defines a chamber for containing desiccant, the member including first and second parts which when fitted together define the chamber for containing desiccant. The first part has an outer surface provided with at least one of an internal or external spline and the second part has an inner surface provided with at least one of the other of an internal or external spline, where the splines (28, 36) are dimensioned and/or spaced so as, on fitting together the first and second parts (14, 16), rotationally to fix the first and second parts and define spaces therebetween.

27 Claims, 5 Drawing Sheets

INHALATION DEVICE

This is a continuation of International Patent Application No. PCT/SE98/00462, with an international filing date of Mar. 13, 1998, now pending.

BACKGROUND

The present invention relates to a powder inhaler and a method of constructing the same.

A number of powder inhalers are known which use different systems for introducing a dose of powder into an air stream. Typically, the powder is inhaled into the lungs of a patient in order to treat, for example, asthma.

One such powder inhaler is disclosed in EP-A-0237507. This inhaler comprises an inhalation channel and a mouthpiece comprising an air chamber and an outlet nozzle, which together define a flow path through which a stream of air is drawn during inhalation by a user. This inhaler further comprises means for introducing powder into the inhalation channel. During inhalation, air is first drawn into and through the inhalation channel so as to pick up powder. The stream of air containing powder is then drawn through the air chamber and out of the outlet nozzle of the mouthpiece.

Powder inhalers are, however, particularly susceptible to the effects of moisture and should therefore include a desiccant, such as silica gel, to absorb any moisture. It will of course be appreciated that it is a requirement that the desiccant be contained entirely separate from the powder to be inhaled so as to avoid contamination of the powder.

In powder inhalers of the kind which comprise an inhaler body and a grip portion at one end thereof, which grip portion is rotatable relative to the inhaler body so as to provide a dose of powder for inhalation, it has been proposed to provide a chamber in the grip portion for containing desiccant. In one proposed construction the grip portion comprises first and second parts which fit together to define a chamber; the first and second parts having cooperating splines to lock the same in the rotational sense. There is, however, one major drawback with this proposed construction in that, when fitting together the first and second parts, particles of desiccant may become lodged between the splines and prevent correct assembly.

It is thus an aim of the present invention to provide a powder inhaler having a construction which allows the parts thereof that define the chamber for containing desiccant to be fitted in a sure and reliable manner when enclosing desiccant.

SUMMARY OF THE INVENTION

Accordingly, the present invention provides an inhaler for administering powder by inhalation which comprises a member that defines a chamber for containing desiccant, the member comprising first and second parts which when fitted together define the chamber for containing desiccant, wherein the first part has an outer surface provided with at least one of an internal or external spline and the second part has an inner surface provided with at least one of the other of an internal or external spline, the splines being dimensioned and/or spaced so as, on fitting together the first and second parts, rotationally to fix the same and define spaces therebetween.

Preferably, the splines are dimensioned and/or spaced so as rotationally to fix the first and second parts irrespective of the relative angular relationship therebetween on fitting.

More preferably, the splines are defined by a plurality of projections provided to the outer and inner surfaces respectively of the first and second parts, and, compared to notional surfaces complete with projections, the outer surface of the first part provided with one of external or internal splines has $n_1$ notional projections missing between adjacent projections, $n_1$ being an integer greater or equal to one, and the inner surface of the second part provided with one of the other of external or internal splines has $n_2$ notional projections missing between adjacent projections, $n_2$ being an integer greater than $n_1$ and satisfying the relationships $(n_1+1).k_1+1=(n_2+1).k_2$ and $(n_1+1).k_3=(n_2+1).k_4$, where $k_1$, $k_2$, $k_3$ and $k_4$ are zero or integers greater than zero and $k_2$ is less than $k_4$.

Preferably, the at least one external spline and the at least one internal spline are of different radial dimension.

Preferably, the first and second parts comprise cooperating detent means for holding the same together on fitting and the splines are dimensioned and/or spaced relative to the cooperating detent means such that, when the first and second parts are fitted together, the at least one external spline is engaged within the at least one internal spline before any resistance to further insertion is caused by the cooperating detent means.

Preferably, the splines are dimensioned and/or spaced such that the axes of the first and second parts are substantially relatively angularly immovable before any resistance to further insertion is caused by the cooperating detent means.

Preferably, the at least one internal spline extends from a position sufficiently near to the peripheral edge of the surface in which the same is provided that, on fitting together the first and second parts, the splines engage before any resistance to further insertion is caused by the cooperating detent means.

Preferably, the relative lengths and positions of the splines are such that at least one-third of the length of each of the external and internal splines is engaged before any resistance to further insertion is caused by the cooperating detent means.

Preferably, the cooperating detent means comprise an at least part circumferential groove and an at least part circumferential ridge which is configured to engage therewithin.

Preferably, the at least part circumferential ridge is provided on the outer surface of the first part and the at least part circumferential groove is provided in the inner surface of the second part.

More preferably, the at least part circumferential groove is provided in the inner surface of the second part between the peripheral edge of the inner surface and the at least one spline provided to the inner surface.

Preferably, the at least one external spline is about three-quarters of the length of the at least one internal spline.

Preferably, the outer surface of the first part is provided with at least one external spline and the inner surface of the second part is provided with at least one internal spline.

Preferably, the inhaler further comprises an inhaler body and a mouthpiece from which powder is in use inhaled, the inhaler body housing a dosing mechanism for providing a dose of powder for inhalation.

More preferably, the member comprises a grip portion for operating the dosing mechanism.

Yet more preferably, the grip portion is rotatably mounted to the inhaler body.

Still yet more preferably, the inhaler body comprises one of an at least part circumferential ridge or an at least part circumferential groove and the grip portion comprises the other of the at least part circumferential ridge or at least part circumferential groove, the at least part circumferential ridge being configured to engage within the at least part circumferential groove.

Preferably, at least a part of a wall of the chamber adjacent the inhaler body is permeable to moisture.

Preferably, an outer surface of the second part has a knurled or ridged surface which can be gripped by a user.

Preferably, the one of the first and second parts which is provided with the at least one internal spline includes at least one element which is disposed so as to be abutted by at least one of the at least one external spline when the first and second parts are fitted together.

Preferably, at least one of the at least one internal spline is bridged at the forward end in the direction of fitting by an element at least one of which is abutted by the at least one external spline when the first and second parts are fitted together.

More preferably, each element is formed of a material which is deformed by the respective external spline.

The present invention also provides a method of constructing an inhaler for administering powder by inhalation which comprises a member that defines a chamber for containing desiccant, the method comprising the steps of: providing first and second parts having respectively an outer surface and an inner surface, which when fitted together define the chamber for containing desiccant; providing the outer surface of the first part with at least one of an internal or external spline and the inner surface of the second part with at least one of the other of an internal or external spline, the splines being dimensioned and/or spaced so as, on fitting together the first and second parts, rotationally to fix the same and define spaces therebetween; and fitting the first and second parts together to define the chamber for containing desiccant.

Preferably, the method further comprises the step of providing the first and second parts with cooperating detent means for holding the same together on fitting, wherein the splines are dimensioned and/or spaced relative to the cooperating detent means such that, when the first and second parts are fitted together, the at least one external spline is engaged within the at least one internal spline before any resistance to further insertion is caused by the cooperating detent means.

In this way, the first and second parts may be put together with the internal and external splines interlocking before any significant force need be applied. With the splines interlocking, and, therefore, the first and second parts aligned, a force may then be applied to engage the detent means and hence axially fix the first and second parts without damaging the splines. With the splines engaging, the first and second parts are disposed with the axes thereof parallel, such that, when the first and second parts are driven together, the first and second parts move squarely and the bottom peripheral edge of the first part cannot be driven into the side of the second part.

In the inhaler of the present invention the chamber is formed easily by merely pressing together the first and second parts. In particular, the construction of the inhaler of the present invention ensures that the significant force required to clip the first and second parts together need not be applied until the first and second parts are aligned and significantly engaged. In other words, during assembly, the first and second parts would not be forced together in a misaligned state.

Preferred embodiments of the present invention will now be described hereinbelow by way of example only with reference to the accompanying drawings.

DETAILED DESCRIPTION OF THE PREFERRED EMBODIMENTS

Figure 1:
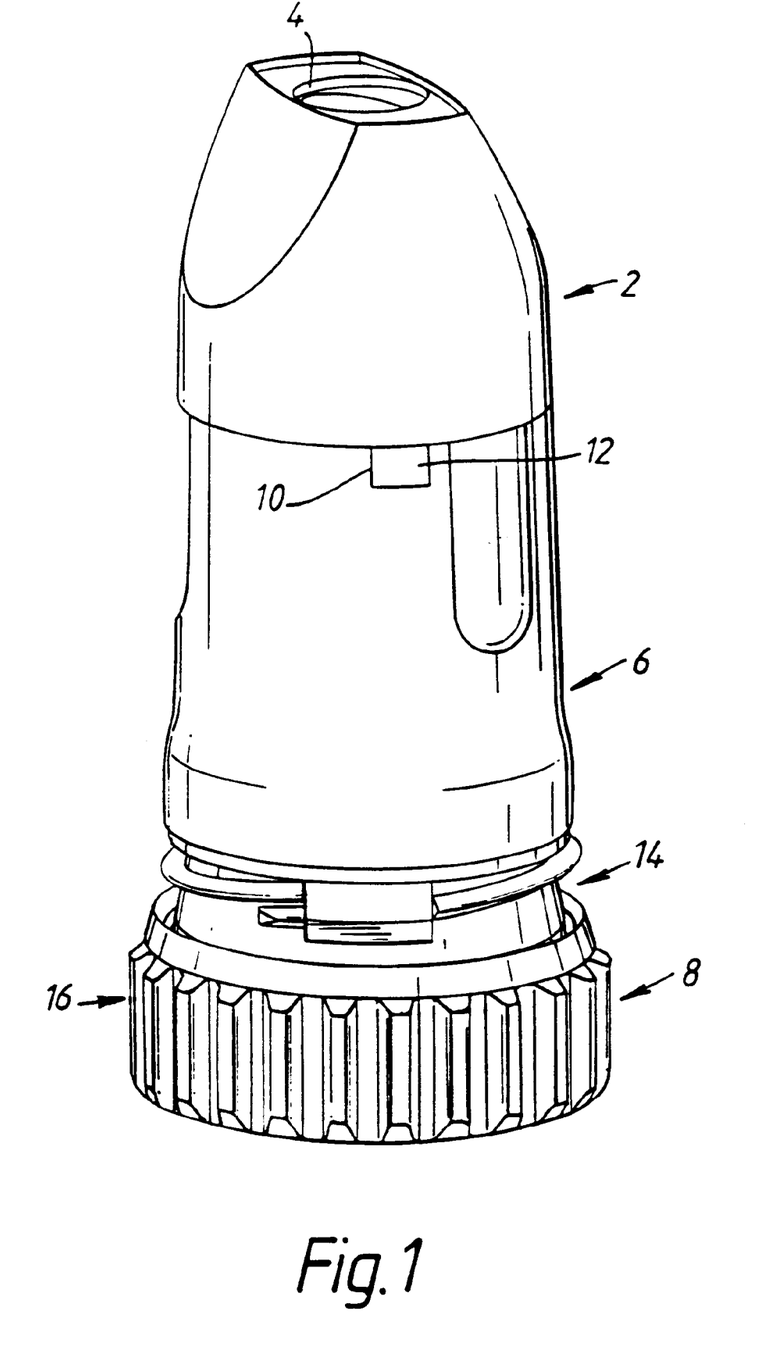
FIG. 1 illustrates a perspective view of a powder inhaler in accordance with a first embodiment of the present invention.

FIG. 1 illustrates a powder inhaler in accordance with a first embodiment of the present invention.

The inhaler comprises a mouthpiece 2 comprising an outlet nozzle 4, an inhaler body 6 and a rotatable grip portion 8 for operating a dosing mechanism disposed in the inhaler body 6 for providing doses of powder for inhalation. The inhaler body 6 is provided with an opening 10 which is filled with a window 12 through which an indicating wheel (not illustrated) is visible so as to provide an indication as to the usage of the inhaler.

In use, the grip portion 8 is first rotated in one sense, in this embodiment in the counter-clockwise sense when viewed from above, through a predetermined angle relative to the inhaler body 6 and then rotated in the opposite, clockwise, sense back to the original position. This action operates the dosing mechanism to provide a dose of powder for inhalation. The user then takes the mouthpiece 2 in the lips and inhales so as to draw powder into the lungs.

Figure 2:
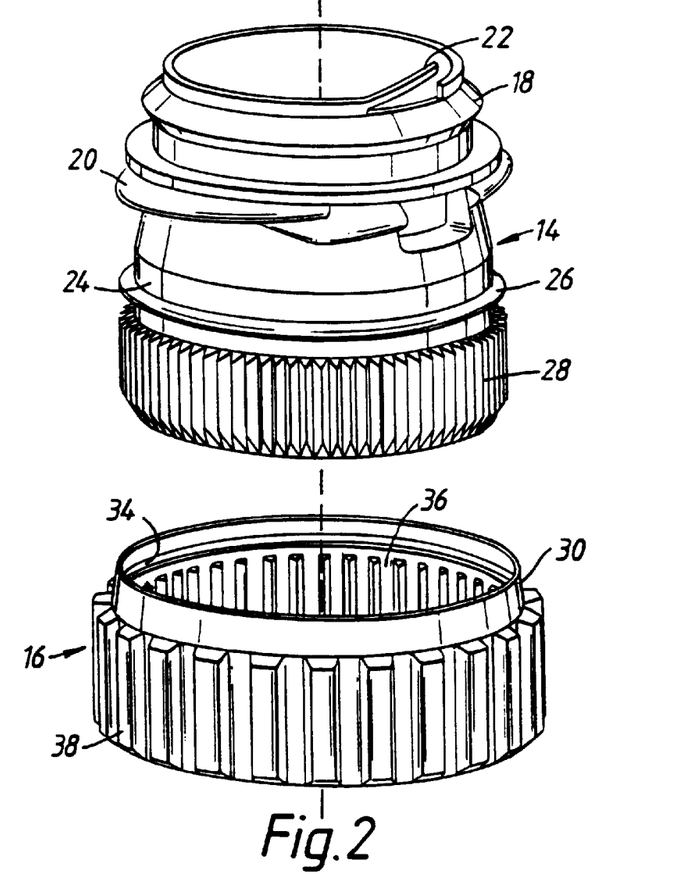
FIG. 2 illustrates in exploded view the component parts of the grip portion of the inhaler of FIG. 1, the components having a common central longitudinal axis.

The grip portion 8 comprises first and second hollow parts 14, 16 which are mutually configured so as to define an enclosed chamber 17 for containing desiccant when fitted together.

The first part 14 comprises a circumferential ridge 18 disposed about the outer surface of one, the upper, end thereof to which the inhaler body 6 is clipped and external threads 20 to which a cap (not illustrated) having corresponding internal threads is screwed so as to cover the mouthpiece 2 and the inhaler body 6 and thus form a tight seal. The first part 14 further comprises an upwardly-directed resiliently-biased arm 22 disposed at the periphery of the upper end thereof, which arm 22, on rotation of the grip portion 8, engages part of the dosing mechanism so as to provide a dose of powder for inhalation. The first part 14 yet further comprises a tubular section 24, in this embodiment of generally cylindrical cross-section, one, the upper, end of which is closed by a wall (not illustrated) which is permeable to moisture. In a preferred embodiment the wall is formed of cardboard. The outer surface of the tubular section 24 includes a circumferential ridge 26 and a plurality of external splines 28, in this embodiment radial projections of triangular cross-section.

The second part 16 comprises a tubular section 30, in this embodiment of generally cylindrical cross-section, one, the lower, end of which is closed by a wall 32. The inner surface of the tubular section 30 includes a circumferential groove 34 at the upper end thereof and a plurality of internal splines 36, in this embodiment of quadrilateral cross-section with outwardly-flaring flanks defined by radial projections of triangular cross-section. The outer surface of the tubular section 30 includes a plurality of axially-directed ridges 38 which are gripped by a user on rotation of the grip portion 8. In another embodiment the outer surface of the tubular section 30 could be knurled. In this embodiment the inner dimension of the tubular section 30 is configured so as to be a close radial fit over the tubular section 24 of the first part 14.

With this construction, the first and second parts 14, 16 are clipped together on locating the ridge 26 in the groove 34; continuous relative rotation of the first and second parts 14, 16 being prevented by the mating splines 28, 36.

The splines 28, 36 are configured, in terms of axial position and axial length, so as to be substantially entirely interengaged before the upper end of the tubular section 30 meets the ridge 26. In practice, it is sufficient for the internal splines 36 to extend near to the upper end of the tubular section 30, though how near is dependent of course upon how near the external splines 28 extend to the lower end of the tubular section 24. If the external splines 28 are relatively long, the internal splines 36 need only be relatively short, and, conversely, if the external splines 28 are relatively short, the internal splines 36 must be relatively long. It will of course be appreciated that the splines 28, 36 can have any dimension and spacing which are such as to fix the first and second parts 14, 16 rotationally relative to one another. In a preferred embodiment the splines 28, 36 are configured so as to fix the first and second parts 14, 16 rotationally relative to one another irrespective of the relative angular positions thereof when fitted together.

In this embodiment, in which the splines 28, 36 on the first and second parts 14, 16 are defined by radial projections of the same dimension, the number of projections defining the external splines 28 is different to the number of projections defining the internal splines 36, thereby giving rise to a different circumferential spacing of the projections. Preferably, as in this embodiment, the number of projections defining the external splines 28 is greater than the number of projections defining the internal splines 36. By way of example, the first part 14 could be provided with thirty-six equi-spaced projections defining the external splines 28 and the second part 16 provided with twenty-four equi-spaced projections defining the internal splines 36. In this way, when the first and second parts 14, 16 are fitted together, axially-extending spaces exist between the splines 28, 36. Thus, if particles of desiccant happen to pass between the splines 28, 36 during fitting together of the first and second parts 14, 16, those desiccant particles will not impede assembly, but rather fall into the spaces. This construction is particularly advantageous where the inhaler is assembled automatically by machine, since, if spaces are not provided between the splines 28, 36 and particles of desiccant become lodged therebetween, it is likely that when the assembly machine forces the first and second parts 14, 16 together, the splines 28, 36 will become damaged, causing either the first and second parts 14, 16 to be deformed and/or the ridge 26 and groove 34 not to be properly engaged. It will, however, be appreciated that in practice for reasons of production some of the projections defining the splines 28, 36 may be omitted. For instance, in the example given above having thirty-six equi-spaced external splines 28, one or more, typically four, thereof may be omitted leaving one or more sections of the outer surface of the first part 14 without splines 28.

Figures 3, 14:
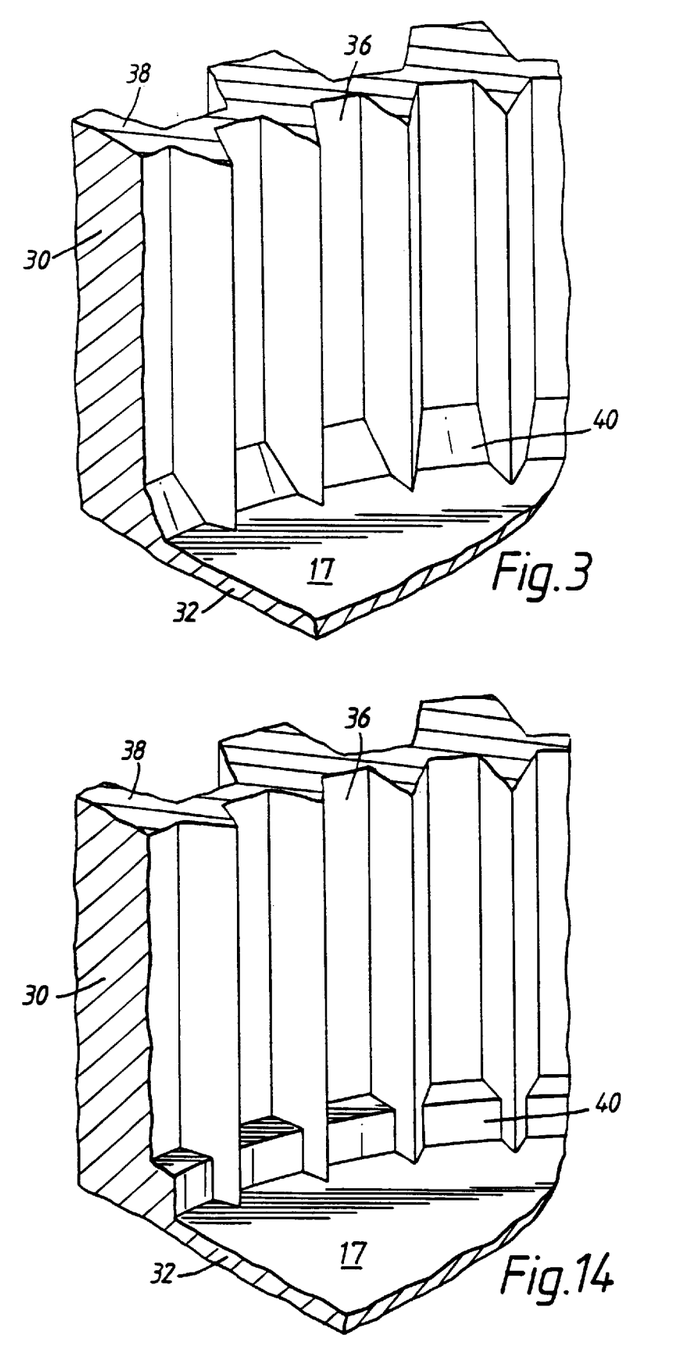
FIG. 3 illustrates a fragmentary part sectional view of the inner surface of one component part of the grip portion of the inhaler of FIG. 1.
FIG. 14 illustrates a fragmentary part sectional view of the inner surface of one component part of the grip portion of an inhaler in accordance with a second embodiment of the present invention.

As illustrated in FIG. 3, the ends of the internal splines 36 adjacent the end wall 32, in this embodiment at the junction between the tubular section 30 and the end wall 32, include elements 40 which bridge the flanks thereof. In this embodiment the elements 40 are of triangular cross-section with the hypotenuse facing upwardly and inwardly relative to the inner surface of the tubular section 30. It is not necessary that all of the internal splines 36 be bridged by elements 40. However, for ease of moulding and optimum effect, the elements 40 are provided by a circumferential bead. The purpose of the elements 40 is as follows. When the external splines 28 are passed into the internal splines 36, the lower ends of the external splines 28 contact the respective elements 40 before the ridge 26 is located in the groove 34. In this way, when the ridge 26 is located in the groove 34 and the first and second parts 14, 16 are fitted together, the external splines 28 cut into the respective elements 40 so as further to anchor the first and second parts 14, 16 together, both in a rotational and an axial sense.

FIGS. 4 to 13 illustrate configurations of the external and internal splines 28, 36 of the first and second parts 14, 16 which provide axially-extending spaces into which particles of desiccant can pass. It will be noted that for ease of understanding FIGS. 4 to 13 illustrate the surfaces to which the splines 28, 36 are provided as planar surfaces and not as generally cylindrical surfaces as in the described embodiment. It will also be noted that FIGS. 4 to 13 illustrate in chain line the positions of the notional projections which would be located between the actual projections defining the splines 28, 36 if the surfaces to which the splines 28, 36 are provided were to be provided completely with equi-spaced projections of the same dimension.

Figure 4:
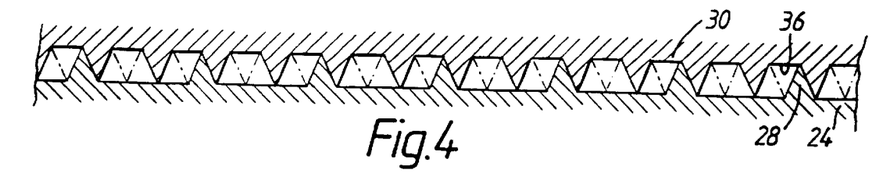
FIGS. 4 to 13 illustrate possible configurations of the external and internal splines of the component parts of the grip portion of the inhaler of FIG. 1.
Figure 5:
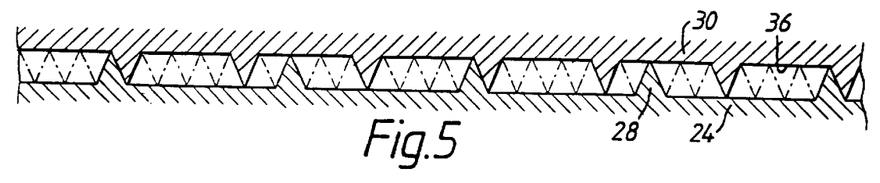
Figure 6:
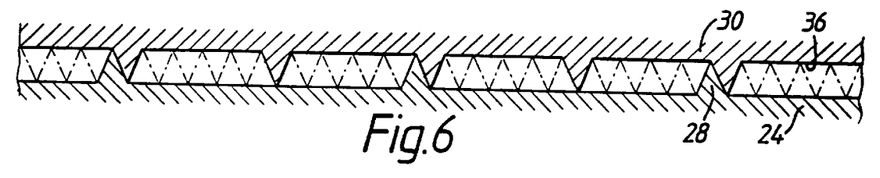
Figure 7:
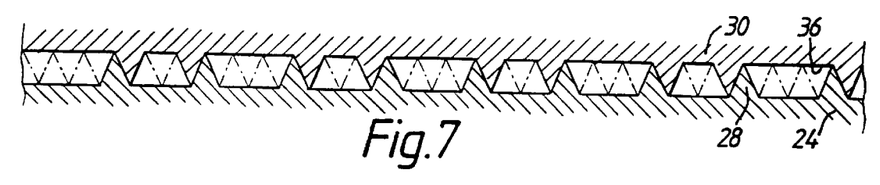
Figure 8:
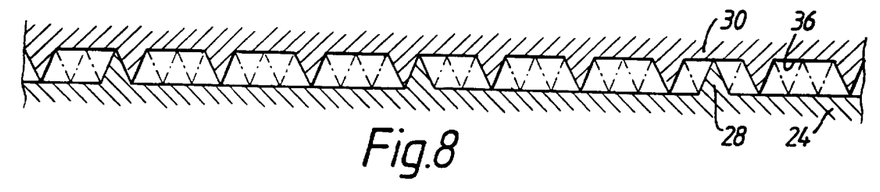
Figure 9:
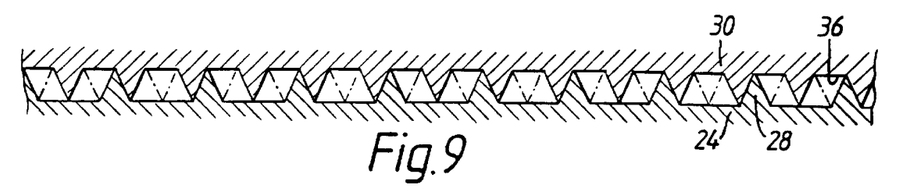
Figure 10:
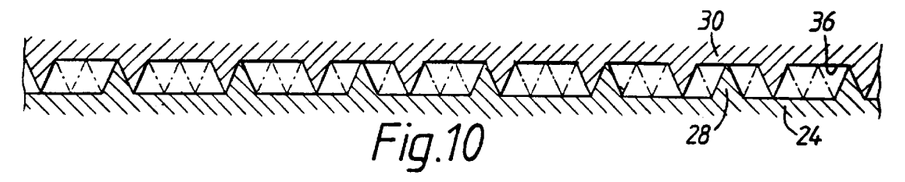
Figure 11:
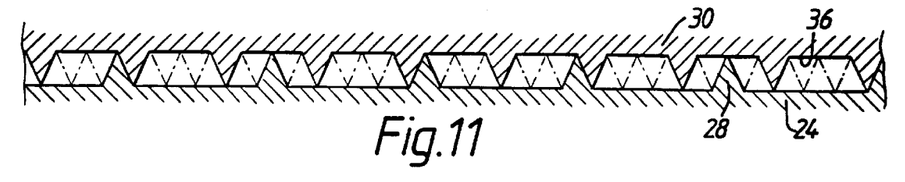
Figure 12:
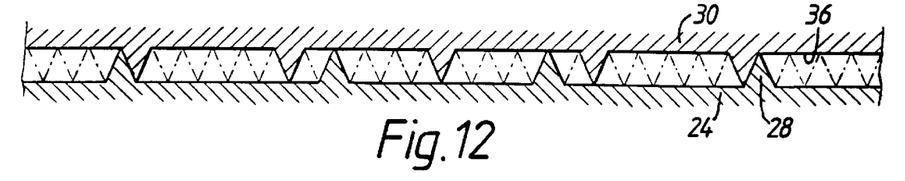
Figure 13:
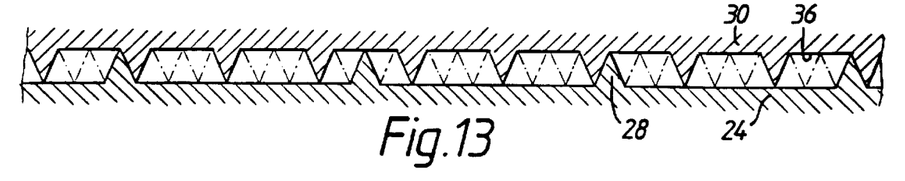

Whilst FIGS. 4 to 13 illustrate possible configurations of the external and internal splines 28, 36 which provide axially-extending spaces into which particles of desiccant can pass, it will be noted that FIGS. 4 to 6 illustrate configurations in which the first and second parts 14, 16 are relatively movable to a limited extent and FIGS. 7 and 8 illustrate configurations in which the first and second parts 14, 16 are fixed relative to one another only for particular relative positions thereof. FIGS. 9 to 13, however, illustrate configurations in which the first and second parts 14, 16 are fixed in position relative to one another irrespective of the positional relationship therebetween on fitting.

In order for the first and second parts 14, 16 to be fixed in position relative to one another irrespective of the positional relationship thereof on fitting, the projections defining one of the external or internal splines 28, 36 have to be arranged such that one projection defining the one of an external or internal spline 28 abuts the flank of a projection defining the other of an external or internal spline 28, 36 facing in one direction and the next projection defining the one of an external or internal spline 28, 36 which abuts a projection defining the other of an external or internal spline 28, 36 abuts the flank thereof facing in the other direction. The simplest case is where adjacent projections satisfy this relationship, as in the configurations illustrated for example in FIGS. 9 and 10. Thus, where the projections defining the splines 28, 36 have a repeat, then in each repeat the projections defining one of the external or internal splines 28, 36 are arranged such that the first two projections which abut projections defining the other of the external or internal splines 28, 36 abut oppositely-directed surfaces thereof.

In a preferred embodiment, if $n_1$ represents the number of notional projections missing between the actual projections on the outer surface of the first part 14 and $n_2$ represents the number of notional projections missing between the actual projections on the inner surface of the second part 16, then for the first and second parts 14, 16 to be relatively fixed in position irrespective of the positional relationship therebetween on fitting, the following relationships $(n_1+1).k_1+1=(n_2+1).k_2$ and $(n_1+1).k_3=(n_2+1).k_4$ have to be satisfactory where $k_1, k_2, k_3$ and $k_4$ are zero or integers greater than zero and $k_2$ is less than $k_4$. This relationship assumes a regular spacing of projections defining the splines 28, 36, but it will be appreciated that irregular configurations of projections are within the scope of the invention.

FIG. 14 illustrates the inner surface of the second part 16 of the grip portion 8 of an inhaler in accordance with a second embodiment of the present invention. This inhaler is almost identical in structure to the inhaler of the above-described first embodiment and differs only in that the elements 40 bridging the internal splines 36 are of square cross-section, with one surface of the elements 40 being parallel to the inner surface of the tubular section 30.

Figure 15:
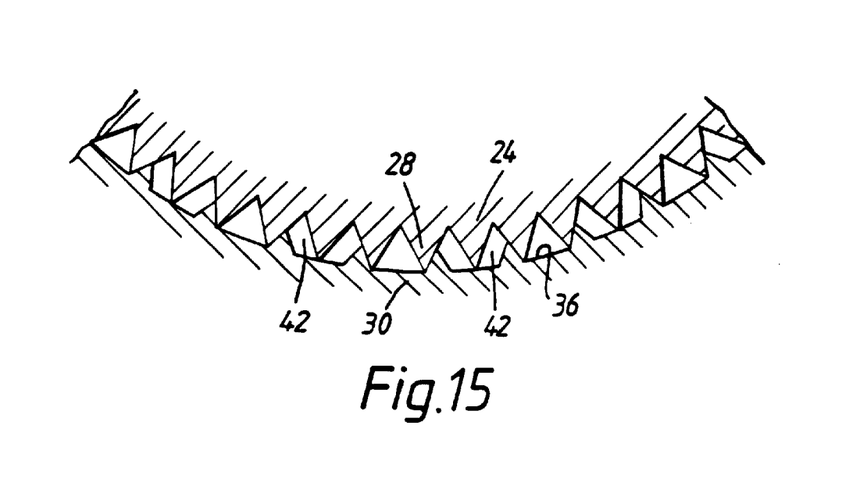
FIG. 15 illustrates a fragmentary horizontal sectional view through the grip portion of a powder inhaler in accordance with a third embodiment of the present invention.

FIG. 15 illustrates a fragmentary horizontal sectional view through the grip portion 8 of a powder inhaler in accordance with a third embodiment of the present invention. This inhaler is almost identical in structure to the inhaler of the above-described first embodiment and differs only in that the external splines 28 are of different, in this embodiment larger, radial dimension to the internal splines 36 such that when the first and second parts 14, 16 are fitted together axially-extending spaces 42 exist between the splines 28, 36. In this way, if particles of desiccant happen to pass between the splines 28, 36 during assembly, those desiccant particles will not impede assembly, but rather fall into the spaces 42.

Finally, it will be understood by a person skilled in the art that the present invention has been described in its preferred embodiments and can be modified in many different ways without departing from the scope of the invention as defined in the appended claims.

In another embodiment the circumferential ridge 26 could be disposed at the lower end of the tubular section 24, that is forward of the external splines 28 in the direction of fitting, and the circumferential groove 34 disposed at the lower end of the tubular section 30, that is forward of the internal splines 36 in the direction of fitting. Thus, in the same manner as the above-described embodiments, the ridge 26 will not engage in the groove 34 until after the splines 28, 36 are interlocked.

In yet another embodiment the circumferential ridge 26 could be replaced by a circumferential groove and the circumferential groove 34 replaced by a circumferential ridge.

In still yet another embodiment the first part 14 could be provided with internal splines and the second part 16 provided with external splines.

What is claimed is:

1. An inhaler for administering powder by inhalation which comprises a member that defines a chamber for containing desiccant, the member comprising first and second parts which when fitted together define the chamber for containing desiccant, wherein the first part has an outer surface provided with at least one of an internal or external spline and the second part has an inner surface provided with at least one of the other of an internal or external spline, the splines being dimensioned and spaced and the first and second parts fitted together, wherein the first and second parts define a plurality of spaces therebetween, such that any desiccant caught between the splines may be contained within the spaces, and wherein said plurality of spaces may be achieved by varying only the dimensions of said splines on said outer surface relative to the dimensions of said splines on said inner surface, or by varying only the spacing between said splines on said outer surface relative to said splines on said inner surface, or by varying both the dimensions and the spacing of said splines on said outer surface relative to said splines on said inner surface.

2. The inhaler according to claim 1, wherein the splines are dimensioned and spaced so as to prevent full relative rotation between the first and second parts irrespective of the relative angular relationship therebetween on fitting, wherein the prevention of full relative rotation may be achieved by varying only the dimensions of said splines on said outer surface relative to the dimensions of said splines on said inner surface, or by varying only the spacing between said splines on said outer surface relative to said splines on said inner surface, or by varying both the dimensions and the spacing of said splines on said outer surface relative to said splines on said inner surface.

3. The inhaler according to claim 2, wherein the splines are defined by a plurality of projections provided to the outer and inner surfaces respectively of the first and second parts, and, compared to notional surfaces complete with projections, the outer surface of the first part provided with one of external or internal splines has $n_1$ notional projections missing between adjacent projections, $n_1$ being an integer greater than or equal to one, and the inner surface of the second part provided with one of the other of external or internal splines has $n_2$ notional projections missing between adjacent projections, $n_2$ being an integer greater than $n_1$ and satisfying the relationships $(n_1+1).k_1+1=(n_2+1).k_2$ and $(n_1+1).k_3+(n_2+1).k_4$, where $k_1, k_2, k_3$ and $k_4$ are zero or integers greater than zero and $k_2$ is less than $k_4$.

4. The inhaler of claim 3, wherein both the first part and the second part have a generally cylindrical shape, where the outer surface of the first part has a diameter less than or equal to a diameter of the inner surface of the second part, and the first and second parts, when fitted together, share a common central axis.

5. The inhaler according to claim 1, wherein the at least one external spline and the at least one internal spline are of different radial dimension.

6. The inhaler according to claim 1, wherein the first and second parts comprise cooperating detent structures for holding the first and second parts together, and the splines are dimensioned and spaced relative to the cooperating detent structures such that, when the first and second parts are fitted together, the at least one external spline is engaged within the at least one internal spline before any resistance to further insertion is caused by the cooperating detent means, wherein the engagement of the at least one external spline within the at least one internal spline may be achieved by varying only the dimensions of said splines on said outer surface relative to the dimensions of said splines on said inner surface, or by varying only the spacing between said splines on said outer surface relative to said splines on said inner surface, or by varying both the dimensions and the spacing of said splines on said outer surface relative to said splines on said inner surface.

7. The inhaler according to claim 6, wherein the cooperating detent structures comprise an at least part circumferential groove and an at least part circumferential ridge which are configured to engage each other.

8. The inhaler according to claim 7, wherein the at least part circumferential ridge is provided on the outer surface of the first part and the at least part circumferential groove is provided in the inner surface of the second part.

9. The inhaler according to claim 8, wherein the at least part circumferential groove is provided in the inner surface of the second part between the peripheral edge of the inner surface and the at least one spline provided to the inner surface.

10. The inhaler according to claim 1, wherein the splines are dimensioned and spaced such that the first and second parts are substantially relatively angularly immovable about a common central longitudinal axis before any resistance to further insertion is caused by the cooperating detent structures, wherein the relative angular immovability may be achieved by varying only the dimensions of said splines on said outer surface relative to the dimensions of said splines on said inner surface, or by varying only the spacing between said splines on said outer surface relative to said splines on said inner surface, or by varying both the dimensions and the spacing of said splines on said outer surface relative to said splines on said inner surface.

11. The inhaler according to claim 1, wherein the at least one internal spline extends from a position sufficiently near to the peripheral edge of the surface in which the internal spline is provided that, on fitting together the first and second parts, the internal and external splines engage before any resistance to futher insertion is caused by the cooperating detent structures.

12. The inhaler according to claim 1, wherein the relative lengths and positions of the splines are such that at least one-third of the length of each of the external and internal splines is engaged before any resistance to further insertion is caused by the cooperating detent structures.

13. The inhaler according to claim 1, wherein the at least one external spline is about three-quarters of the length of the at least one internal spline.

14. The inhaler according to claim 1, wherein the outer surface of the first part is provided with at least one external spline and the inner surface of the second part is provided with at least one internal spline.

15. The inhaler according to claim 1, further comprising an inhaler body and a mouthpiece from which powder is in use inhaled, the inhaler body housing a dosing mechanism for providing a dose of powder for inhalation.

16. The inhaler according to claim 15, wherein the member defining the chamber for containing desiccant comprises a grip portion for operating the dosing mechanism.

17. The inhaler according to claim 16, wherein the grip portion is rotatably mounted to the inhaler body.

18. The inhaler according to claim 17, wherein the inhaler body comprises one of an at least part circumferential ridge or an at least part circumferential groove and the grip portion comprises the other of the at least part circumferential ridge or at least part circumferential groove, the at least part circumferential ridge being configured to engage within the at least part circumferential groove.

19. The inhaler according to claim 13, wherein at least a part of a wall of the chamber adjacent the inhaler body is permeable to moisture.

20. The inhaler according to claim 15, wherein an outer surface of the second part has a knurled or rigid surface which can be gripped by a user.

21. The inhaler according to claim 1, wherein the one of the first and second parts which is provided with the at least one internal spline includes at least one element which is disposed so as to be abutted by at least one of the at least one external spline when the first and second parts are fitted together.

22. The inhaler according to claim 21, wherein the element disclosed to be abutted is formed of a material which is deformed by the respective external spline.

23. The inhaler according to claim 1, wherein at least one of the at least one internal spline is bridged at the forward end in the direction of fitting by an element at least one of which is abutted by the at least one external spline when the first and second parts are fitted together.

24. The inhaler of claim 1, wherein both the first part and the second part have a generally cylindrical shape, where the outer surface of the first part has a diameter less than or equal to a diameter of the inner surface of the second part, and the first and second parts, when fitted together, share a common central axis.

25. A dry powder inhaler having an element which defines a chamber for containing a desiccant, said element comprising a first part, shaped in the form of a cylinder, having a first detent structure and an outer cylindrical surface having a first spline;

a second part, shaped in the form of a cylinder, having a second detent structure sized and shaped to mate with the first detent structure and having an inner cylindrical surface having a second spline sized and shaped to mate with the first spline;

where the outer surface of the first part has a diameter less than or equal to a diameter of the inner surface of the second part, and, when the first part and the second part are fitted together,
 (i) the first part and the second part share a common central longitudinal axis;
 (ii) the first and second detent structures engage each other, preventing the first part from sliding relative to the second part in the direction of the common central axis; and
 (iii) the first spline and second spline engage each other, defining spaces therebetween, such that any desiccant caught between the splines may be contained within the spaces, and preventing the first part from rotating relative to the second part about the common central axis.

26. A method of constructing an inhaler for administering powder by inhalation which comprises a member that defines a chamber for containing desiccant, the method comprising the steps of:

providing a first part having an outer surface and a second part having an inner surface, which when fitted together define the chamber for containing desiccant;

providing the outer surface of the first part with at least one of an internal or external spline and the inner surface of the second part with at least one of the other of an internal or external spline, the splines being dimensioned and spaced fitting together the first and second parts, wherein said first and second parts define a plurality of spaces therebetween, such that any desiccant caught between said splines may be contained within the spaces, and wherein defining said plurality of spaces may be achieved by varying only the dimensions of said splines on said outer surface relative to the dimensions of said splines on said inner surface, or by varying only the spacing between said splines on said outer surface relative to said splines on said inner surface, or by varying both the dimensions and the spacing of said splines on said outer surface relative to said splines on said inner surface and fitting the first and second parts together to define the chamber for containing desiccant.

27. The method according to claim 26, further comprising the step of providing the first and second parts with cooperating detent structures for holding the first and second parts together on fitting, wherein the splines are dimensioned and spaced relative to the cooperating detent structures such that, when the first and second parts are fitted together, the at least one external spline is engaged within the at least one internal spline before any resistance to further insertion is caused by the cooperating detent structures, wherein the engagement of the at least one external spline with the at least one internal spline may be achieved by varying only the dimensions of said splines on said outer surface relative to the dimensions of said splines on said inner surface, or by varying only the spacing between said splines on said outer surface relative to said splines on said inner surface, or by varying both the dimensions and the spacing of said splines on said outer surface relative to said splines on said inner surface.

* * * * *